US010028846B2

(12) United States Patent
Flohr et al.

(10) Patent No.: US 10,028,846 B2
(45) Date of Patent: Jul. 24, 2018

(54) METHOD FOR CHECKING CERAMIC BALL HEADS FOR HIP-JOINT PROSTHESES

(71) Applicant: CeramTec GmbH, Plochingen (DE)

(72) Inventors: Markus Flohr, Esslingen (DE);
Carsten Upmann, Stuttgart (DE);
Hendrik Bertmaring, Esslingen (DE)

(73) Assignee: CeramTec GmbH, Plochingen (DE)

( * ) Notice: Subject to any disclaimer, the term of this patent is extended or adjusted under 35 U.S.C. 154(b) by 0 days.

(21) Appl. No.: 14/378,996

(22) PCT Filed: Feb. 13, 2013

(86) PCT No.: PCT/EP2013/052890
§ 371 (c)(1),
(2) Date: Aug. 19, 2014

(87) PCT Pub. No.: WO2013/120906
PCT Pub. Date: Aug. 22, 2013

(65) Prior Publication Data
US 2015/0013469 A1 Jan. 15, 2015

(30) Foreign Application Priority Data
Feb. 16, 2012 (DE) .................. 10 2012 202 372

(51) Int. Cl.
*G01N 3/08* (2006.01)
*A61F 2/76* (2006.01)
(Continued)

(52) U.S. Cl.
CPC ................ *A61F 2/76* (2013.01); *A61F 2/468* (2013.01); *G01N 3/08* (2013.01); *G01N 3/10* (2013.01);
(Continued)

(58) Field of Classification Search
CPC ........... G01N 3/08; G01N 3/10; G01N 29/14; G01N 3/12; A61F 2/42; A61F 2/30;
(Continued)

(56) References Cited

U.S. PATENT DOCUMENTS 4,619,659 A * 10/1986 Witzel ................ A61F 2/30907
623/23.36
5,025,595 A * 6/1991 Orain ..................... B24B 11/00
451/28

(Continued)

FOREIGN PATENT DOCUMENTS

DE 44 11 508 A1 10/1995
EP 1 449 501 A1 8/2004
(Continued)

OTHER PUBLICATIONS

English translation of WO 2009/068234A1, which is of record with the USPTO.

*Primary Examiner* — Harshad R Patel
*Assistant Examiner* — Octavia Hollington
(74) *Attorney, Agent, or Firm* — Norton Rose Fulbright US LLP

(57) ABSTRACT

The invention relates to a method for checking ceramic ball heads (3) for hip-joint prostheses which have a receiving space (8) with a conical side face with a clamping cone angle γ and a cone inlet (7) and are subjected to a pressure in order to check areas of the receiving space (8). To ensure that all the checked ball heads (3) also remain functionally ready for relevant, oblique in vivo load situations without suffering damage, it is proposed that only the area of the cone inlet (7) is subjected to a radial force perpendicular to the longitudinal axis of the ball head (3).

14 Claims, 1 Drawing Sheet

(51) Int. Cl.
*A61F 2/46* (2006.01)
*G01N 3/10* (2006.01)
*A61F 2/36* (2006.01)
*A61F 2/30* (2006.01)

(52) U.S. Cl.
CPC ... *A61F 2/3609* (2013.01); *A61F 2002/30332* (2013.01); *A61F 2002/365* (2013.01); *A61F 2002/762* (2013.01); *A61F 2310/00179* (2013.01)

(58) Field of Classification Search
CPC ...... A61F 2/46; A61F 2/36; A61F 2/76; A61F 2/32; A61F 2/34
USPC ............ 73/826, 587; 623/23.12, 22.15
See application file for complete search history.

(56) References Cited

U.S. PATENT DOCUMENTS

| | | | | |
|---|---|---|---|---|
| 5,625,154 | A * | 4/1997 | Matsuhiro | F01L 3/02 73/760 |
| 5,647,667 | A * | 7/1997 | Bast | G01N 3/60 374/57 |
| 6,176,140 | B1 * | 1/2001 | Autenrieth | A61F 2/34 623/908 |
| 6,383,227 | B1 * | 5/2002 | Baroud | A61F 2/3601 623/23.11 |
| RE37,964 | E * | 1/2003 | Prats | A61F 2/3609 623/23.11 |
| 6,564,647 | B1 * | 5/2003 | Richter | A61F 2/468 73/818 |
| 6,901,811 | B2 | 6/2005 | Baebler et al. | |
| 8,151,464 | B2 * | 4/2012 | Orend | B29C 65/08 29/505 |
| 2002/0193882 | A1 * | 12/2002 | Koller | A61F 2/4684 623/23.12 |
| 2008/0262626 | A1 * | 10/2008 | Raugel | A61F 2/30734 623/22.15 |
| 2014/0033820 | A1 * | 2/2014 | Wakayama | G01N 3/08 73/587 |

FOREIGN PATENT DOCUMENTS

JP  2007-307011 A  11/2007
WO  2009/068234 A1  6/2009

* cited by examiner

METHOD FOR CHECKING CERAMIC BALL HEADS FOR HIP-JOINT PROSTHESES

FIELD OF THE INVENTION

This application is a § 371 of International Application No. PCT/EP2013/052890 filed Feb. 13, 2013, and claims priority from German Patent Application No. 10 2012 202 372.0 filed Feb. 16, 2012.

The invention relates to a method for checking ceramic ball heads for hip-joint prostheses, which have a receiving space with a conical side face having a clamping cone angle γ and a cone inlet and are subjected to a pressure for checking areas of the receiving space.

BACKGROUND OF THE INVENTION

The required minimum strength of modular, ceramic ball heads is ensured by means of a so-called proof test (100%-check). Thereby the conical area of the ball head is hydraulically stressed. This is described in DE 44 11 508 C2.

In view of the special geometrics of modular ball heads, under relevant, oblique in-vivo loads, high tensions can occur in the area of the cone inlet.

According to present-day knowledge there is still no method (proof test), which checks the cone inlet of modular ball heads and guarantees the required minimum strength within the scope of a 100%-check for this area. 100%-check means, that ball heads with defects break up in the proof test, so that only flawless ball heads pass the proof test.

OBJECTS AND SUMMARY OF THE INVENTION

The object of the invention is to improve a method for checking ceramic ball heads for hip-joint prosthesis so that all tested ball heads remain operational without damage also in relevant, oblique in-vivo load situations.

This object is achieved according to the invention which relates to a method for checking ceramic ball heads for hip-joint prosthesis, which have a receiving space with a conical side face with a clamping cone angle y and a cone inlet and are subjected to a pressure for testing areas of the receiving space, is characterized in that only the area of the cone inlet is subjected to a radial force perpendicular to the longitudinal axis of the ball head.

DETAILED DESCRIPTION

The method according to the invention for checking ceramic ball heads for hip-joint prostheses, which have a receiving space with a conical side face having a clamping cone angle γ and a cone inlet and are subjected to a pressure for checking areas of the receiving space, is distinguished in that only the area of the cone inlet is subjected to a radial force perpendicular to the longitudinal axis of the ball head. Thereby all tested ball heads remain operational without damage also in in-vivo, relevant oblique load situations.

For testing, preferably a conical sleeve is pressed into the receiving space at a cone angle α, wherein the cone angle α is greater than the clamping cone angle γ. In this way, only the cone inlet is stressed.

In one embodiment the cone angle α is selected in the range from 7° to 30°, preferably 18° and the distance between clamping cone angle γ and cone angle α is to be selected between minimum 2° and maximum 25°.

It has been proven that the sleeve is preferably closed on the circumferential surface thereof and preferably is made from a copper alloy, preferably brass.

Preferably a conical pressure stamp is pressed at a cone angle α identical to the sleeve cone angle axially with a force F into the sleeve.

In one embodiment it is ensured, that the friction between sleeve and pressure stamp is lower than the friction between sleeve and ball head.

Preferably the pressure stamp is fabricated from steel and preferably is surface-hardened.

In one embodiment hydraulic pressure is applied to the inner surface of the sleeve for testing.

An device for carrying out the method according to the invention is characterized in that the device comprises a counter bearing, a conical sleeve and a pressure stamp, wherein all are arranged on a common longitudinal axis and the sleeve and pressure stamp are moveable on the longitudinal axis, and the sleeve is located between the pressure stamp and the counter bearing and the cone angle α is greater than the clamping angle γ of a ball head to be checked.

Preferably the sleeve has cone angle α, with which the cone angle of the pressure stamp is identical.

The invention is further explained hereafter by means of Figures.

Figure 1:
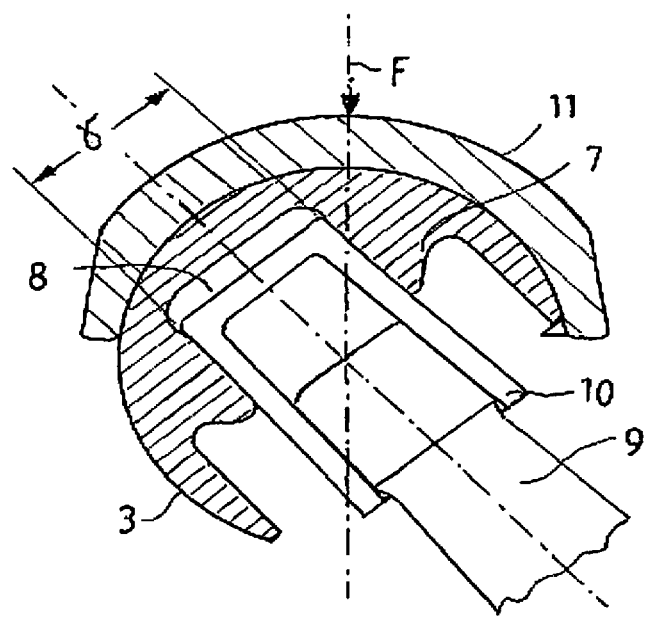
FIG. 1 is shows the area of a cone inlet in which high tensions in the area of the cone inlet are generated by radially acting forces.

The invention describes a proof test for the area of the cone inlet 7 (see FIG. 1), in which high tensions in the area of the cone inlet 7 are generated by radially acting forces. This can take place hydraulically or mechanically. FIG. 1 shows a shaft 9 of a hip-joint prosthesis, which is implanted in the femur. A spacer sleeve 10 is disposed on the shaft head of shaft 9, the outer surface thereof engaging in the receiving space 8 of the ball head 3 and is anchored via a conical clamp at the clamping cone angle γ. The ball head 3 is inserted as revolvable in a ceramic guide shell (11).

Figure 2:
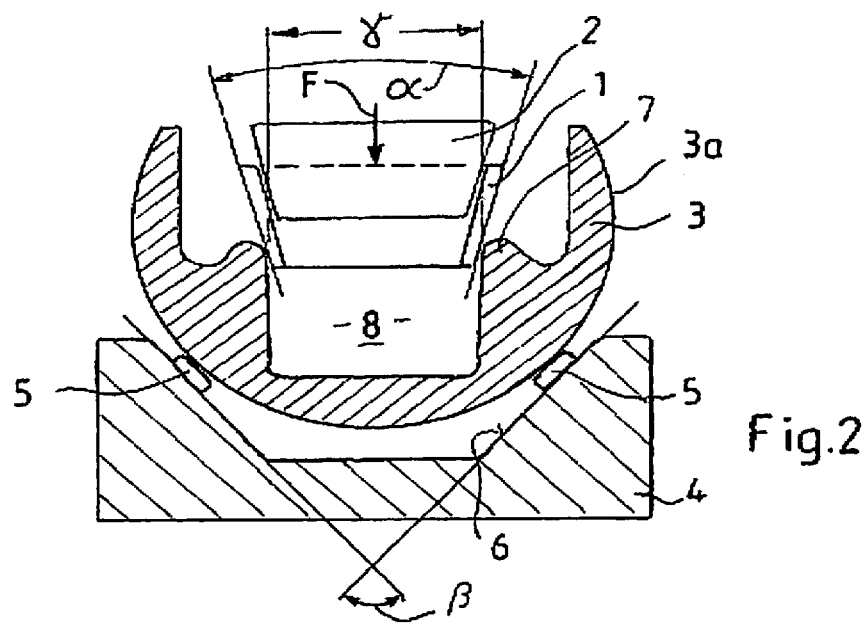
FIG. 2 shows an embodiment according to the invention showing that the mechanical load unit of the proof test consists of at least two components.

The mechanical load unit of the proof test consists of at least two components 1, 2 (see FIG. 2), which makes possible a movement relative to one another. Component 1 is a closed conical sleeve and component 2 is a conical pressure stamp, which is inserted in component 2 and in the test is pressed axially with a force F (see FIG. 2) into component 1, whereby the cone inlet 7 is impacted radially with a force.

The deflection of the radial force F in the radial direction is increased by the relative movement of the two components 1 and 2. The two components 1, 2 are ideally shaped conically on the outer surface thereof. The cone angle α should be greater than the clamping cone angle γ of the ball head. For a clamping cone angle γ of 5° 42'30" the cone of the pressure stamp should be selected in the range from 7° to 30°, ideally an angle of 18° is used. For all angle variations a difference between clamping cone angle γ and angle α of the pressure stamp of at least 2° to at most 25° is generally recommended.

The material of the conical sleeve (component 1) should be sufficiently ductile, to ensure adjustment of the sleeve on the ball head. Additionally, the material of the sleeve must have sufficient strength to withstand the shearing load. Copper alloys come into question as possible materials. Ideally the sleeve (component 1) consists of brass.

The conical pressure stamp (component 2) must be significantly harder than the sleeve. Ideally the pressure stamp is surface-hardened. In order to ensure the relative movement between pressure stamp and sleeve, the surface of the conical pressure stamp must be smooth. Ideally the surface of the conical pressure stamp is polished, ($R_a$<0.2). Thus it is crucial, that the friction between component 1 and component 2 is significantly less than between component 1 and the ball head. The sleeve is always termed component 1 and vice versa. The pressure stamp is always termed as component 2 and vice versa.

To apply the load via a hydraulic system instead of the conical pressure stamp, the inner surface of the sleeve is exposed to hydraulic pressure. For this purpose, sealing may be effected with an O-ring. The sleeve 1 can be conical or cylindrical either on the inside or outside.

To perform the proof test, the ball head 3 with outer surface 3a is placed on a counter bearing 4 having a conical recess 6. The angle of the conical recess 6 is designated as β. The ball head 3 is thereby advantageously disposed via a ring 5 on the conical recess 6 of the counter bearing 4.

For the proof test, component 1, e.g. the sleeve, is placed with inserted component 2, e.g. the pressure stamp, onto the cone inlet 7 of the ball head 3. The outer cone angle α of component 1 is greater than the clamping cone angle γ of the receiving space 8 in ball head 3, so that component 1 exerts a force only on the cone inlet 7.

For testing, component 2 is pressed axially with force F in the direction of the ball head. Since component 1 is disposed only on the cone inlet 7 of the ball head 3, the effect of an exerted force is checked only in this area.

Through the relative movement of component 2 to component 1, the force on the cone inlet 7 is increased.

Component 1, e.g. the sleeve is preferably designed to be closed over the entire circumference and, for example, is not slit. It has surprisingly been discovered that slit sleeves cause breaking of the ball head with less application of force than unslit sleeves.

The invention claimed is:

1. A method comprising checking a ceramic ball head for a hip-joint prostheses, which has a receiving space with a conical side face with a clamping cone angle γ and a cone inlet and is subjected to a pressure for testing areas of the receiving space, wherein only an area of the cone inlet of the ceramic ball head is subjected to a radial force perpendicular to a longitudinal axis of the ball head,
wherein the checking is a proof test which checks the cone inlet of modular ball heads and guarantees a required minimum strength within a of a 100%-check for the area, where 100%-check means that ball heads with a defect break up in the proof test so that only ball heads having no defects pass the proof test;
wherein a conical sleeve with a cone angle α is pressed into the receiving space for the checking, wherein the cone angle α is greater than the clamping cone angle γ; and
wherein the sleeve comprises a copper alloy.

2. A method according to claim 1, wherein a conical sleeve with a cone angle α is pressed into the receiving space for the checking, wherein the cone angle α is greater than the clamping cone angle γ.

3. A method according to claim 2, wherein the cone angle α is selected in a range of from 7° to 30°, and a difference between clamping cone angle γ and cone angle α is between a minimum of 2° and a maximum of 25°.

4. A method according to claim 3, wherein the cone angle α is 18°.

5. A method according to claim 3, wherein a conical pressure stamp with a cone angle α identical to that of the sleeve is pressed axially with a force F into the sleeve.

6. A method according to claim 5, wherein the friction between sleeve and pressure stamp is less than a friction between sleeve and ball head.

7. A method according to claim 5, wherein the pressure stamp is made from a steel.

8. A method according to claim 7, wherein the steel is surface-hardened.

9. A method according to claim 5, wherein the sleeve has cone angle α, which is the same as the cone angle of the pressure stamp.

10. A method according to claim 2, wherein the sleeve is closed on a circumferential surface thereof.

11. A method according to claim 2, wherein the cone angle α is selected in a range of from 7° to 30°, and a difference between clamping cone angle γ and cone angle α is between a minimum of 2° and a maximum of 25°.

12. A method according to claim 11, wherein the copper alloy is brass.

13. A method according to claim 2, wherein an inner surface of the sleeve is subjected to hydraulic pressure for the checking.

14. A method comprising checking a ceramic ball head for a hip-joint prostheses with a device comprising:
a counter bearing having a conical recess;
a conical sleeve having a conically shaped outer surface; and
a conical pressure stamp; wherein the counter bearing, the conical sleeve and the pressure stamp are arranged on a longitudinal axis
wherein the conical sleeve and the pressure stamp are displaceable on the longitudinal axis; and
wherein the conical sleeve is disposed between the pressure stamp and the counter bearing, wherein the ceramic ball head has a receiving space with a conical side face with a clamping cone angle γ and a cone inlet, comprising the steps of:
subjecting the ball head to a pressure for a testing area of the receiving space,
wherein only an area of the cone inlet is subjected to a radial force perpendicular to the longitudinal axis of the ball head,
wherein the checking is a proof test which checks the cone inlet of modular ball heads and guarantees a required minimum strength within the scope of a 100%-check for the area,
where 100%-check means that ball heads with a defect break up in the proof test so that only ball heads having no defects pass the proof test.

\* \* \* \* \*